United States Patent [19]
Andino et al.

[11] Patent Number: 6,008,233
[45] Date of Patent: Dec. 28, 1999

[54] (1S,2S)-1-(4-HYDROXYPHENYL)-2-(4-HYDROXY-4-PHENYLIPIPERIDIN-1-YL)-1-PROPANOLMETHANESULFONATE TRIHYDRATE

[75] Inventors: Marta M. Andino, Gales Ferry; Terry G. Sinay, Preston; Eugene F. Fiese, Ledyard, all of Conn.

[73] Assignee: Pfizer Inc, New York, N.Y.

[21] Appl. No.: 09/011,426

[22] PCT Filed: Jun. 20, 1996

[86] PCT No.: PCT/IB96/00592

§ 371 Date: May 7, 1998

§ 102(e) Date: May 7, 1998

[87] PCT Pub. No.: WO97/07098

PCT Pub. Date: Feb. 27, 1997

Related U.S. Application Data

[60] Provisional application No. 60/002,238, Aug. 11, 1995.

[51] Int. Cl.$^6$ .................................................... A01N 43/40
[52] U.S. Cl. ............................................. 514/327; 546/217
[58] Field of Search .............................. 546/217; 514/327

[56] References Cited

U.S. PATENT DOCUMENTS 5,185,343  2/1993  Chenard .
5,272,160  12/1993  Chenard .

FOREIGN PATENT DOCUMENTS

WO 96/06081  2/1996  WIPO .

*Primary Examiner*—John Kight
*Assistant Examiner*—Raymond Covington
*Attorney, Agent, or Firm*—Peter C. Richardson; Paul H. Ginsburg; Bryan C. Zielinski

[57] ABSTRACT

The invention relates to the trihydrate of the mesylate salt of (1S,2S)-1-(4-hydroxyphenyl)-2-(4-hydroxy-4-phenylpiperidin-1-yl)-1-propanol, pharmaceutical compositions containing said compound and methods of treating disorders of the central nervous system by administering said compound.

10 Claims, 2 Drawing Sheets

(1S,2S)-1-(4-HYDROXYPHENYL)-2-(4-HYDROXY-4-PHENYLIPIPERIDIN-1-YL)-1-PROPANOLMETHANESULFONATE TRIHYDRATE

This application claims benefit of Provisional Application 60/002,238 filed Aug. 11, 1995.

This invention relates to the novel and clinically advantageous trihydrate of the methanesulfonate salt of (1S,2S)-1-(4-hydroxyphenyl)-2-(4-hydroxy-4-phenylpiperidin-1-yl)-1-propanol (hereinafter referred to as "the mesylate salt trihydrate"). This mesylate salt trihydrate, as well as the corresponding anhydrous mesylate salt and free base of (1S,2S)-1-(4-hydroxyphenyl)-2-(4-hydroxy-4-phenylpiperidin-1-yl)-1-propanol (hereinafter referred to, respectively, as "the anhydrous mesylate" and "the free base") exhibit activity as NMDA (N-methyl-D-aspartic acid) receptor antagonists and are useful in the treatment of epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions, urinary incontinence and degenerative CNS (central nervous system) disorders such as stroke, Alzheimer's disease, Parkinson's disease and Huntington's disease.

The free base, the anhydrous mesylate and methods of preparing them are referred to, generically, in U.S. Pat. No. 5,185,343, which issued on Feb. 9, 1993. They and their use in treating certain of the above disorders are referred to, specifically, in U.S. Pat. No. 5,272,160, which issued on Dec. 21, 1993. Their use in treating the above disorders is referred to in International Patent Application PCT/IB 95/00380, which designates the United States and was filed on May 18, 1995. Their use in combination with a compound capable of enhancing and thus restoring the balance of excitatory feedback from the ventral lateral nucleus of the thalamus into the cortex to treat Parkinson's disease is referred to in International Patent Application PCT/IB 95/00398, which designates the United States and was filed on May 26, 1995. The foregoing U.S. patents and patent applications are incorporated herein by reference in their entireties.

NMDA is an excitatory amino acid. The excitatory amino acids are an important group of neurotransmitters that mediate excitatory neurotransmission in the central nervous system. Glutamic acid and aspartic acid are two endogenous ligands that activate excitatory amino acid (EAA) receptors. There are two types of EAA receptors, ionotropic and metabotropic, which differ in their mode of signal transduction. There are at least three distinct ionotropic EAA receptors characterized by the selective agonist that activates each type: the NMDA, the AMPA (2-amino-3-(5-methyl-3-hdyroxyisoxazol-4-yl)propanoic acid) and the kainic acid receptors. The ionotropic EAA receptors are linked to ion channels that are permeable to sodium and, in the case of NMDA receptors, calcium. Metabotropic receptors, linked to phosphoinositide hydrolysis by a membrane associated G-protein, are activated by quisqualic acid, ibotenic acid, and (1S,3R)-1-aminocyclopentane 1,3-dicarboxylic acid.

The NMDA receptor is a macromolecular complex consisting of a number of distinct binding sites that gate on ion channels permeable to sodium and calcium ions. Hansen and Krogsgaard-Larson, *Med. Res. Rev.*, 10, 55–94 (1990). There are binding sites for glutamic acid, glycine, and polyamines, and a site inside the ion channel where compounds such as phencyclidine (PCP) exert their antagonist effects.

Competitive NMDA antagonists are compounds that block the NMDA receptor by interacting with the glutamate binding site. The ability of a particular compound to competitively bind to the NMDA glutamate receptor may be determined using a radioligand binding assay, as described by Murphy et al., *British J. Pharmacol.*, 95, 932–938 (1988). The antagonists may be distinguished from the agonists using a rat cortical wedge assay, as described by Harrison and Simmonds, *British J. Pharmacol.*, 84, 381–391 (1984). Examples of competitive NMDA antagonists include D-2 amino 5-phosphonopentanoic acid (D-AP5), and D2-amino-7-phosphonoheptanoic acid, Schoepp et al., *J. Neur. Transm.*, 85, 131–143 (1991).

This invention also relates to a method treating of mammals suffering from Parkinson's disease which comprises administering to said mammal (1S,2S)-trans-2-methyl-2-(4-hydroxy-4-phenylpiperidin-1-yl)-1-hydroxy-1-(4-hydroxyphenyl)ethanol methanesulfonate trihydrate and a compound capable of increasing the excitatory feedback from the ventral lateral nucleus of the thalamus into the cortex, such that the balance of the excitatory feedback from the ventral lateral nucleus of the thalamus into the cortex in said mammal suffering from Parkinson's disease is restored. International Patent Application PCT/IB 95/00398, which is referred to above and incorporated herein by reference in its entirety, refers to the use of the free base and the anhydrous mesylate in combination with such an excitatory feedback enhancing agent to treat Parkinson's disease.

The mesylate trihydrate is substantially superior as a therapeutic agent compared to the anhydrous mesylate. It is a more stable crystalline form than the corresponding anhydrous salt, has a substantially longer shelf life and is less subject to breakdown of the crystal structure due to the inclusion of water in the crystal.

SUMMARY OF THE INVENTION

This invention relates to (1S,2S)-1-(4-hydroxyphenyl)-2-(4-hydroxy-4-phenylpiperidin-1-yl)-1-propanol methanesulfonate trihydrate.

This invention also relates to a pharmaceutical composition for the treatment of a disorder selected from degenerative CNS disorders such as stroke, Alzheimer's disease, Parkinson's disease and Huntington's disease; spinal cord trauma, epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, including a human, comprising an NMDA antagonizing amount of (1S,2S)-1-(4-hydroxyphenyl)-2-(4-hydroxy-4-phenylpiperidin-1-yl)-1-propanol methanesulfonate trihydrate and a pharmaceutically acceptable carrier.

This invention also relates to a pharmaceutical composition for the treatment of a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, including a human, comprising an amount of (1S,2S)-1-(4-hydroxyphenyl)-2-(4-hydroxy-4-phenylpiperidin-1-yl)-1-propanol methanesulfonate trihydrate that is effective in treating such disorder, and a pharmaceutically acceptable carrier.

This invention also relates to a method of treating a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, including a human, comprising administering to said mammal an amount of (1S,2S)-1 (4-hydroxyphenyl)-2-(4-hydroxy-4-phenylpiperidin-1-yl)-1-propanol methane-sulfonate trihydrate that is effective is treating such disorder.

This invention also relates to a method of treating a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, including a human, comprising administering to said mammal an NMDA antagonizing amount of (1S,2S)-1-(4-hydroxyphenyl)-2-(4-hydroxy-4-phenylpiperidin-1-yl)-1-propanol methanesulfonate trihydrate.

This invention relates to a method of treating Parkinson's disease in a mammal, including a human, comprising administering to said mammal a Parkinson's disease treating effective amount of a synergistic combination of (1S,2S)-1-(4-hydroxyphenyl)-2-(4-hydroxy-4-phenylpiperidin-1-yl)-1-propanol methanesulfonate trihydrate and an agent capable of restoring the balance of the excitatory feedback from the ventral lateral nucleus of the thalamus into the cortex.

This invention also relates to a method of treating Parkinson's disease in a mammal, including a human, comprising treating said mammal with a Parkinson's disease treating effective amount of a synergistic combination of the trihydrate of (1S,2S)-1-(4-hydroxyphenyl)-2-(4-hydroxy-4-phenylpiperidin-1-yl)-1-propanol methanesulfonate trihydrate and an excitatory feedback enhancing agent selected from the group consisting of dopamine agonists, dopamine D1 agonists, dopamine D2 agonists, dopamine/β-adrenergic receptor agonists, dopamine/5-HT uptake inhibitor/5-HT-1A agonists, dopamine/opiate agonists, adrenoreceptor agonists, α2-adrenergic antagonist/dopamine agonists, α2-adrenergic/dopamine D2 agonists, dopamine uptake inhibitors, monoamine oxidase inhibitors, monoamine oxidase-B inhibitors, catecholamethyl, transferases (COMT) inhibitors and levodopa.

Figure 1:
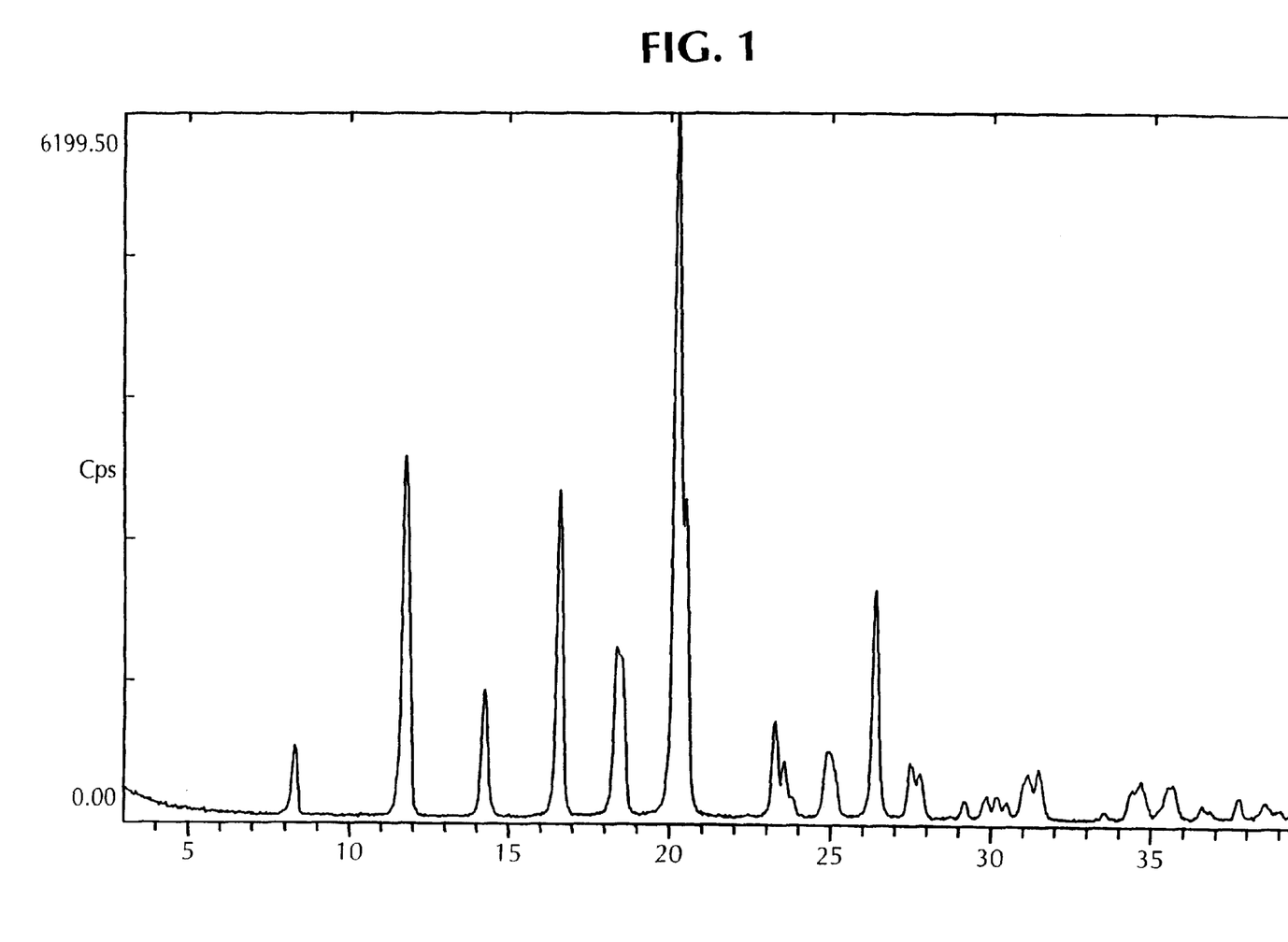
FIG. 1 depicts the X-ray powder diffraction spectrum of the mesylate trihydrate (taken on a Siemens D 5000 diffractometer after equilibration of the anhydrous mesylate at 81% relative humidity ("RH")), expressed as intensity (CPS) versus diffraction angle (two-theta degrees).

Tables 1 and 2 below identify selected peaks from the spectra of FIGS. 1 and 2, respectively, by diffraction angle (two-theta), d-spacing (d), relative intensity (ref. int.) and maximum intensity (max. int.).

Table 1

X-RAY POWDER DIFFRACTION DATA FOR THE MESYLATE TRIHYDRATE

TABLE 1

| Two-Theta (degrees) | D-spacing (degrees) | Max. Int. (counts/sec) | Rel. Int. (%) |
|---|---|---|---|
| 8.290 | 10.6563 | 668.50 | 10.78 |
| 11.786 | 7.5026 | 3202.00 | 51.65 |
| 14.267 | 6.2027 | 1160.00 | 18.71 |
| 16.618 | 5.3302 | 2910.00 | 46.94 |
| 18.473 | 4.7989 | 1513.00 | 24.41 |
| 20.261 | 4.3792 | 6199.50 | 100.00 |
| 23.272 | 3.8190 | 893.50 | 14.41 |
| 23.640 | 3.7604 | 493.00 | 7.95 |
| 24.965 | 3.5838 | 633.00 | 10.21 |
| 26.380 | 3.3757 | 2042.50 | 32.95 |
| 27.755 | 3.2116 | 445.50 | 7.19 |
| 29.165 | 3.0594 | 214.00 | 3.45 |
| 29.839 | 2.9919 | 259.50 | 4.19 |
| 30.160 | 2.9607 | 256.50 | 4.14 |
| 30.480 | 2.9303 | 207.50 | 3.35 |
| 31.106 | 2.8728 | 449.50 | 7.25 |
| 31.480 | 2.8395 | 493.50 | 7.96 |
| 33.564 | 2.6678 | 125.50 | 2.02 |
| 34.649 | 2.5867 | 388.00 | 6.26 |
| 35.574 | 2.5216 | 358.00 | 5.77 |
| 36.568 | 2.4553 | 193.50 | 3.12 |
| 37.680 | 2.3853 | 254.50 | 4.11 |
| 38.507 | 2.3360 | 215.00 | 3.47 |
| 38.920 | 2.3121 | 158.00 | 2.55 |
| 39.320 | 2.2895 | 129.00 | 2.08 |

Table 2

X-RAY POWDER DIFFRACTION DATA FOR THE ANHYDROUS MESYLATE

TABLE 2

| Two-Theta (degrees) | D-spacing (degrees) | Max. Int. (counts/sec) | Rel. Int. (%) |
|---|---|---|---|
| 4.495 | 19.6436 | 149.50 | 9.29 |
| 9.098 | 9.7116 | 1610.00 | 100.00 |
| 9.656 | 9.1524 | 221.00 | 13.73 |
| 11.733 | 7.5362 | 682.50 | 42.39 |
| 12.374 | 7.1472 | 284.50 | 17.67 |
| 12.976 | 6.8167 | 123.00 | 7.64 |
| 13.564 | 6.5229 | 149.50 | 9.29 |
| 14.120 | 6.2671 | 130.50 | 8.11 |
| 14.484 | 6.1106 | 196.00 | 12.17 |
| 15.313 | 5.7814 | 667.00 | 41.43 |
| 16.268 | 5.4440 | 213.50 | 13.26 |
| 17.088 | 5.1847 | 777.00 | 48.26 |
| 17.799 | 4.9791 | 694.00 | 43.11 |
| 18.264 | 4.8535 | 569.50 | 35.37 |
| 18.916 | 4.6876 | 440.00 | 27.33 |
| 19.368 | 4.5791 | 679.50 | 42.20 |
| 19.937 | 4.4498 | 1332.50 | 82.76 |
| 20.743 | 4.2787 | 296.50 | 18.42 |
| 21.357 | 4.1571 | 216.50 | 13.45 |
| 22.410 | 3.9641 | 354.50 | 22.02 |
| 23.056 | 3.8544 | 230.50 | 14.32 |
| 23.672 | 3.7554 | 250.50 | 15.56 |
| 24.725 | 3.5978 | 243.00 | 15.09 |
| 26.024 | 3.4211 | 246.00 | 15.28 |
| 27.098 | 3.2880 | 127.00 | 7.89 |

TABLE 2-continued

X-RAY POWDER DIFFRACTION DATA FOR THE ANHYDROUS MESYLATE

| Two-Theta (degrees) | D-spacing (degrees) | Max. Int. (counts/sec) | Rel. Int. (%) |
|---|---|---|---|
| 28.276 | 3.1535 | 126.50 | 7.86 |
| 28.820 | 3.0953 | 121.00 | 7.52 |
| 30.083 | 2.9681 | 103.00 | 6.40 |
| 32.611 | 2.7435 | 97.00 | 6.02 |
| 33.272 | 2.6905 | 100.50 | 6.24 |
| 34.292 | 2.6128 | 83.50 | 5.19 |
| 38.188 | 2.3548 | 87.50 | 5.43 |

DETAILED DESCRIPTION OF THE INVENTION

Figure 2:
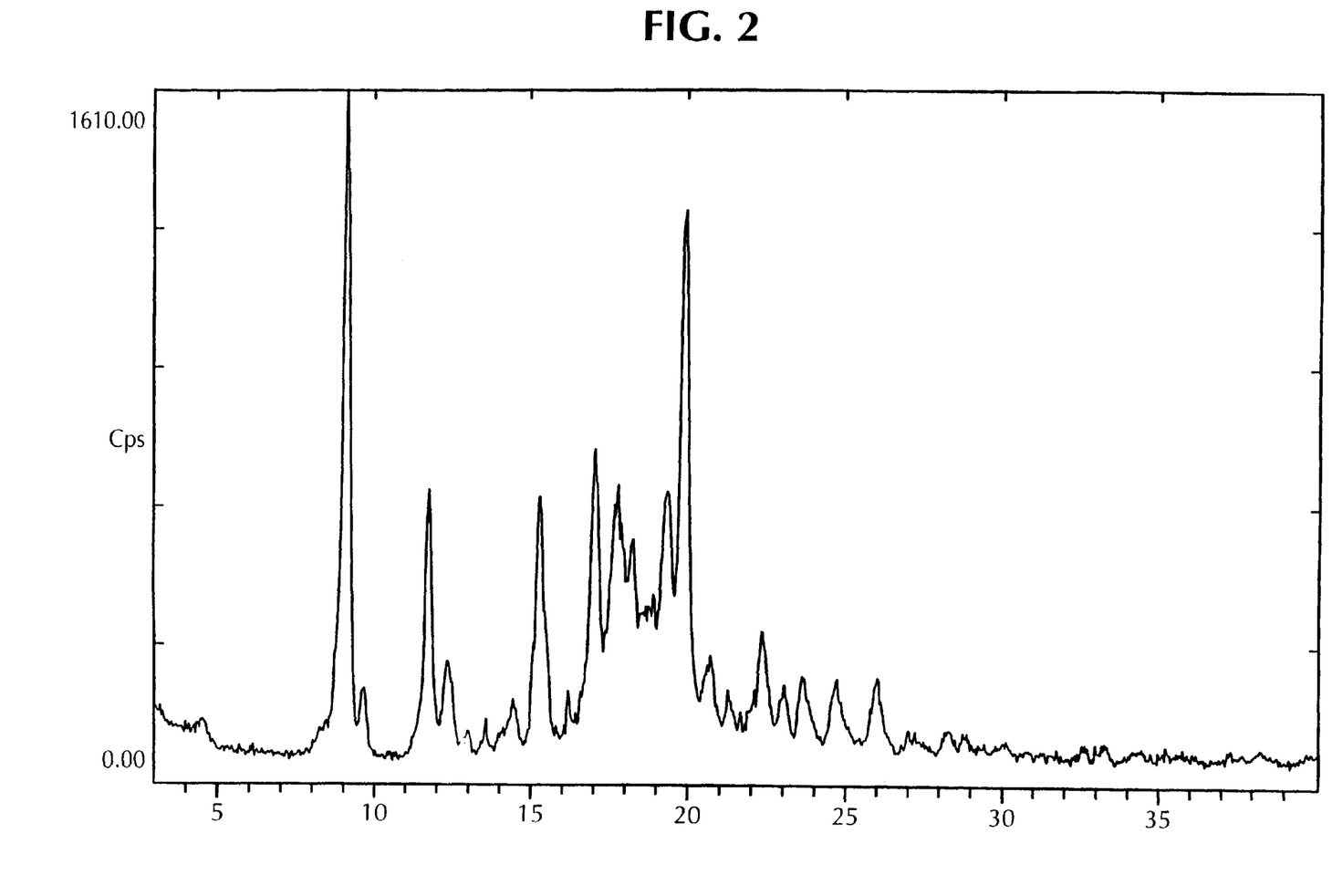
FIG. 2 depicts the X-ray powder diffraction spectrum of the anhydrous mesylate, taken on a Siemens D 5000 diffractometer and expressed as intensity (CPS) versus diffraction angle (two-theta degrees).

The mesylate salt trihydrate is a white crystalline solid that exhibits well defined, narrowed X-ray diffraction peaks (FIG. 1), in contrast to the anhydrous mesylate, which exhibits poor diffraction pattern resolution, a raised background and lack of diffraction peaks at 2θ>26° (FIG. 2). Only one crystalline form has been observed for the trihydrate mesylate. This crystalline form has good solubility in water (25 and 15 mg/mL in pH 3 and 7 aqueous buffered solutions, respectively).

The mesylate salt trihydrate can be prepared by the following method. The free base is dissolved in water at 30° C. To this solution is added at least 1 equivalent of methane sulfonic acid and the resulting mixture is warmed to 60–65° C. The warm solution can be filtered to render it particulate free. The solution is concentrated to approximately 40% of the initial volume, cooled below 10° C., isolated by filtration and dried to a water content (measured Karl Fischer titration) of approximately 11.3%. The resulting crystalline mesylate salt trihydrate can be further purified by recrystallization.

The anhydrous mesylate, when equilibrated in an 81% RH environment, will convert to the mesylate salt trihydrate.

The free base and anhydrous mesylate can be prepared as described in U.S. Pat. No. 5,272,160, which is referred to above and incorporated herein by reference in its entirety. The resolution of racemic 1-(4-hydroxyphenyl)-2-(4-hydroxy-4-phenylpiperidin-1-yl)-1-propanol to form the free base and corresponding (1R,2R) enantiomer is exemplified in Example 1. An alternate method of preparing the free base is described in Example 2, which also exemplifies the synthesis of the mesylate salt trihydrate.

The hygroscopicity of the mesylate salt trihydrate was studied at 0%, 52% and 98% controlled relative humidities (RH's), and under ambient laboratory conditions (24–27° C., 31–64% RH's). No weight change was observed at 52% and 98% RH's or under ambient conditions. Loss of waters of hydration is observed at 0% RH. The weight loss observed at 0% RH was reversible; the anhydrous form quickly equilibrated to the hydrated form when exposed to higher humidities. Weight loss was also observed in bulk stability samples stored in polyethylene bags at 40° C./30% RH (>10% of weight was lost in 9 months).

By contrast, a substantial weight gain was observed for the anhydrous mesylate at ambient conditions, as shown in Table 3 below.

Table 3

HYGROSCOPICITY AT AMBIENT CONDITIONS OF THE ANHYDROUS MESYLATE SALT

TABLE 3

HYGROSCOPICITY AT AMBIENT CONDITIONS OF THE ANHYDROUS MESYLATE SALT

| Weight of Sample | % Difference from Prev. Weighing | % Difference from Initial | Time Since Initial |
|---|---|---|---|
| 0.4974 g | — | — | — |
| 0.4977 g | 0.06 | 0.06 | 1 hours |
| 0.4977 g | 0.00 | 0.06 | 3.5 hours |
| 0.4990 g | 0.26 | 0.32 | 22 hours |
| 0.5002 g | 0.24 | 0.56 | 30.5 hours |
| 0.5070 g | 1.36 | 1.93 | 45.5 hours |
| 0.5102 g | 0.63 | 2.57 | 98 hours |
| 0.5170 g | 1.33 | 3.94 | 170 hours |
| 0.5170 g | 0.00 | 3.94 | 194 hours |
| 0.5171 g | 0.02 | 3.96 | 215 hours |
| 0.5184 g | 0.25 | 4.22 | 246 hours |
| 0.5203 g | 0.37 | 4.60 | 382 hours |
| 0.5193 g | −0.19 | 4.40 | 408 hours |
| 0.5193 g | 0.00 | 4.40 | 533 hours |

Proton and Carbon Nuclear Magnetic Resonance (NMR) Spectra of the Mesylate Salt Trihydrate The proton and carbon NMR spectra of the mesylate sat trihydrate are described below. Chemical shift assignments in $CD_3OD$ (relative to tetramethylsilane (TMS) were made on the basis of $^1H$-$^1H$ Correlated Spectroscopy (COSY), $^1H$-$^{13}C$ Distortionless Enhancement by Polarization Transfer (DEPT), and $^1H$-$^{13}C$ Heteronuclear Chemical Shift Correlation (HETCOR) two-dimensional NMR experiments. The tentative proton and carbon peak assignments are given below and are consistent with the structure of the mesylate salt trihydrate.

| Assignment | $^{13}C$ (δ, ppm) | # Protons | $^1H$ (δ, ppm) |
|---|---|---|---|
| 4' | 159.2 | 0 | — |
| 1''' | 148.2 | 0 | — |
| 1' | 132.6 | 0 | — |
| 2' | 129.8 | 2 | 7.30 (m) |
| 3''' | 129.5 | 2 | 7.38 (t) |
| 4''' | 128.4 | 1 | 7.30 (m) |
| 2''' | 125.6 | 2 | 7.56 (d) |
| 3' | 116.5 | 2 | 6.84 (d) |
| 1 | 73.5 | 1 | 4.66 (d) |
| 4'' | 69.8 | 0 | — |
| 2 | 68.3 | 1 | 3.58 (m) |
| 6''(1) | 48.8 | 2 | 3.32 (d), 3.72 (t) |
| 2''(1) | 43.2 | 2 | 3.58 (m) |
| 4 | 39.5 | 3 | 2.70 (s) |

-continued

| Assignment | $^{13}C$ (δ, ppm) | # Protons | $^{1}H$ (δ, ppm) |
|---|---|---|---|
| 5"(2) | 36.6 | 2 | 2.64 (t), 1.98 (d) |
| 3"(2) | 36.5 | 2 | 2.42 (t), 1.98 (d) |
| 3 | 9.7 | 3 | 1.12(d) |

(1) The 6" and 2" positions are not chemically equivalent; the assignments may be interchangeable.
(2) The 5" and 3" positions are not chemically equivalent the assignments may be interchangeable. The proton splitting pattern at 1.96–2.06 ppm appears as two doublets when acquired on a high-field instrument (500 MHz), but only as a triplet when acquired with a lower field (300 MHz) instrument. This is believed to be due to a salt effect arising from the mesylate.

The mesylate salt trihydrate, similar to the anhydrous mesylate and free base, possesses selective neuroprotective activity, based upon its antiischemic activity and ability to block excitory amino acid receptors. The preferred procedure for evaluating the neuroprotective activity of this compound is that described by Ismail A. Shalaby, et al., in *J. Pharm. and Experimental Therapeutics*, 260, 925 (1992). This article is incorporated herein by reference in its entirety and described below.

Cell culture. Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21). Cells are either plated on 96-well microtiter plates at a density of 80,000 cells per well or on 24-well culture plates at a density of 250,000 cells per well. Cultures are grown at 37° C. in a humidified $Co_2$ tissue culture incubator containing 5% $CO_2$-95% air. Proliferation of nonneuronal cells is controlled by adding 20 μM uridine and 20 μM 5-fluoro-2-deoxyuridine (Sigma Chemical Co., St. Louis, Mo.) from days 6 to 8 of culture. Culture media is exchanged every 2 to 3 days with fresh stock.

Glutamate toxicity. The cultures are assessed for glutamate toxicity 2 to 3 weeks from initial plating. Culture media is removed and cultures rinsed twice with a CSS (in millimolar.): NaCl, 12-; KCl, 5.4; $MgCl_2$, 0.8; $CaCl_2$, 1.8; glucose, 15; and 4-(2-hydroxyethyl)-1-piperazineethanesulfonic acid, 25 mM (pH 7.4). Cultures are then exposed for 15 min (37° C.) to various concentrations of glutamate. After this incubation, cultures are rinsed 3 times with glutamate-free CSS and twice with fresh culture medium without serum. The cultures are then incubated for 20 to 24 hr in serum-free culture medium. The compound being tested is added 2 min before and during the 15-min exposure to glutamate. In some experiments, the compound is added at different times after the glutamate exposure and for the following 20 to 24 hr.

Cell viability is routinely assessed 20 to 24 hours after the excitotoxin exposure by measuring the activity of the cytosolic enzyme LDH. LDH activity is determined from the culture medium of each of the 96 wells of the microtiter plates. A 50-μl sample of the media is added to an equal volume of sodium-phosphate buffer (0.1 M, pH 7.4) containing 1.32 mM sodium pyruvate and 2.9 mM NADH. The 340 nm absorbance of the total reaction mixture for each of the 96 wells is monitored every 5 sec for 2 min by an automated spectrophotometric microtiter plate reader (Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phrase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hours after exposure to 0.1 to 1.0 mM glutamate.

Reagents. DTG can be purchased from Aldrich Chemical Company (Milwaukee, Wis.), and haloperidol from Research Biochemicals Inc. (Natick, Mass.). Spermine can be purchased from Sigma Chemical Co. (St. Louis, Mo.). Horse and fetal bovine serum can be purchased from Hyclone (Logan, Utah). Culture medium, glutamine and penicillin/streptomycin can be purchased from Gibco Co. (Grand Island, N.Y.).

Data analysis. Neurotoxicity can be quantified by measuring the activity of LDH present in the culture medium 20 to 24 hours after glutamate exposure. The increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments is expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of three independent experiments.

The selective neuroprotective antiischemic and excitatory amino acid blocking activities of the mesylate salt trihydrate of this invention render it useful in the treatment of disorders selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence.

In the systemic treatment of such disorders, the dosage is typically from about 0.02 to 250 mg/kg/day (0.001–12.5 g/day in a typical human weighing 50 kg) in single or divided doses, regardless of the route of administration. A more preferred dosage range is from about 0.15 mg/kg/day to about 250 mg/kg/day. Of course, depending upon the exact nature of the illness and the condition of the patient, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The mesylate salt trihydrate may be administered in the form of pharmaceutical compositions together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

EXAMPLE 1

Enantiomeric (1S,2S)- and (1R,2R)-1-(4-Hydroxyphenyl)-2-(4-hydroxy-4-phenylpiperidin-1-yl)-1-propanols

(+)-Tartaric acid (300 mg, 2 mmol) was dissolved in 30 mL warm methanol. Racemic 1S*,2S*-1-(4-hydroxyphenyl)-2-(4-hydroxy-4-phenylpiperidin-1-yl)-1-propanol (655 mg, 2 mmol) was added all at once. With stirring and gentle warming a colorless homogeneous solution was obtained. Upon standing at ambient temperature 24 hours, 319 mg (66%) of a fluffy white precipitate was obtained. This product was recrystallized from methanol to give 263 mg of the (+)-tartrate salt of levorotatory title product as a white solid; mp 206.5–207.5° C.; [alpha]$_D$=−36.2°. This salt (115 mg) was added to 50 mL of saturated NaHCO$_3$. Ethyl acetate (5 mL) was added and the mixture was vigorously stirred 30 minutes. The aqueous phase was repeatedly extracted with ethyl acetate. The organic layers were combined and washed with brine, dried over calcium sulfate, and concentrated. The tan residue was recrystallized from ethyl acetate-hexane to give 32 mg (39%) of white, levorotatory title product; mp 203–204° C.; [alpha]$_D$=−56.9°. Anal. Calc'd. for $C_{20}H_{25}NO_3$: C, 73.37; H, 7.70; N. 4.28. Found: C, 72.61; H, 7.45; N. 4.21.

The filtrate from the (+)-tartrate salt preparation above was treated with 100 mL saturated aqueous NaHCO$_3$ and extracted well with ethyl acetate. The combined organic extracts were washed with brine, dried over calcium sulfate and concentrated to give 380 mg of recovered starting material (partially resolved). This material was treated with (−)-tartaric acid (174 mg) in 30 mL of methanol as above. After standing for 24 hours, filtration gave 320 mg (66%) of product which was further recrystallized from methanol to produce 239 mg of the (−)-tartrate salt of dextrorotatory title product; mp 206.5–207.5° C. [alpha]$_D$=+33.9°. The latter was converted to dextrorotatory title product in the manner above in 49% yield; mp 204–205° C.; [alpha]$_D$=+58.4°. Anal. Found: C, 72.94; H. 7.64; N, 4.24.

EXAMPLE 2

(1S,2S)-1-(4-hydroxyphenyl)-2-(4-hydroxy-4-phenylpiperidin-yl)-1-propanol Methanesulfonate Trihydrate

STEP 1

A 50 gallon glass lined reactor was charged with 17.1 gallons of acetone, 8.65 kilograms (kg) (57.7 mol) of 4'-hydroxypropiophenone, 9.95 kg (72.0 mol) of potassium carbonate and 6.8 liters (l) (57.7 mol) of benzylbromide. The mixture was heated to reflux (56° C.) for 20 hours. Analysis of thin layer chromatography (TLC) revealed that the reaction was essentially complete. The suspension was atmospherically concentrated to a volume of 10 gallons and 17.1 gallons of water were charged. The suspension was granulated at 25° C. for 1 hour. The product was filtered on a 30" Lapp and washed with 4.6 gallons of water followed by a mixture of 6.9 gallons of hexane and 2.3 gallons of isopropanol. After vacuum drying at 45° C., this yielded 13.35 kg (96.4%) of the above-depicted product.

A second run was carried out with 9.8 kg (65.25 mol) of 4'-hydroxypropiophenone using the procedure described above. After drying 15.1 kg (96.3%) of the above-depicted product was obtained.

STEP 2

Under a nitrogen atmosphere, a 100 gallon glass lined reactor was charged with 75 gallons of methylene chloride and 28.2 kg (117.5 mol) of the product from step 1. The solution was stirred five minutes and then 18.8 kg of bromine was charged. The reaction was stirred for 0.5 hours at 22° C. Analysis of TLC revealed that the reaction was essentially complete. To the solution was charged 37 gallons of water and the mixture was stirred for 15 minutes. The methylene chloride was separated and washed with 18.5 gallons of saturated aqueous sodium bicarbonate. The methylene chloride was separated, atmospherically concentrated to a volume of 40 gallons and 60 gallons of isopropanol was charged. The concentration was continued until a pot temperature of 80° C. and final volume of 40 gallons were obtained. The suspension was cooled to 20° C. and granulated for 18 hours. The product was filtered on a 30" Lapp and washed with 10 gallons of isopropanol. After vacuum drying at 45° C., this yielded 29.1 kg (77.6%) of the above-depicted product.

STEP 3

Under a nitrogen atmosphere, a 20 gallon glass lined reactor was charged with 4.90 kg (15.3 mol) of the product from step 2, 7.0 gallons of ethyl acetate, 2.70 kg (15.3 mol) of 4-hydroxy-4-phenylpiperidine and 1.54 kg of triethylamine (15.3 mol). The solution was heated to reflux (77° C.) for 18 hours. The resulting suspension was cooled to 20° C. Analysis by TLC revealed that the reaction was essentially complete. The byproduct (triethylamine hydrobromide salt) was filtered on a 30" Lapp and washed with 4 gallons of ethyl acetate. The filtrate was concentrated under vacuum to a volume of 17 liters. The concentrate was charged to 48 liters of hexane and the resulting suspension granulated for 2 hours at 20° C. The product was filtered on a 30" Lapp and washed with 4 gallons of hexane. After vacuum drying at 50° C., this yielded 4.9 kg (77%) of the above-depicted product.

A second run was carried out with 3.6 kg (11.3 mol) of the product from step 2 using the procedure described above. After drying 4.1 kg (87%) of the above-depicted product was obtained.

STEP 4

"Threo isomer"

Under a nitrogen atmosphere, a 100 gallon glass lined reactor was charged with 87.0 gallons of 2B ethanol and 1.7 kg (45.2 mol) of sodium borohydride. The resulting solution was stirred at 25° C. and 9.4 kg (22.6 mol) of the product from step 3 was charged. The suspension was stirred for 18 hours at 25–30° C. Analysis by TLC revealed that the reaction was essentially complete to the desired threo diastereoisomer. To the suspension was charged 7.8 liters of water. The suspension was concentrated under vacuum to a volume of 40 gallons. After granulating for 1 hour, the product was filtered on a 30" Lapp and washed with 2 gallons of 2B ethanol. The wet product, 9.4 gallons of 2B-ethanol and 8.7 gallons of water were charged to a 100 gallon glass lined reactor. The suspension was stirred at reflux (78° C.) for 16 hours. The suspension was cooled to 25° C., filtered on 30" Lapp and washed with 7 gallons of water followed by 4 gallons of 2B ethanol. After air drying at 50° C., this yielded 8.2 kg (86.5%) of the above-depicted product. This material was recrystallized in the following manner.

A 100 gallon glass lined reactor was charged with 7.9 kg (18.9 mol) of the product from step 3, 20 gallons of 2B ethanol and 4 gallons of acetone. The suspension was heated to 70° C. producing a solution. The solution was concentrated atmospherically to a volume of 15 gallons. The suspension was cooled to 25° C. and granulated for 1 hour. The product was filtered on a 30" Lapp. The wet product and 11.7 gallons of 2B ethanol was charged to a 100 gallon glass lined reactor. The suspension was heated to reflux (78° C.) for 18 hours. The suspension was cooled to 25° C., filtered on a 30" Lapp and washed with 2 gallons of 2B ethanol. After air drying at 50° C. this yielded 5.6 kg (70.6%) of the above-depicted product.

STEP 5

"Threo isomer"

Under a nitrogen atmosphere, a 50 gallon glass lined reactor was charged with 825 g of 10% palladium on carbon (50% water wet), 5.5 kg (13.2 mol) of the product from step 4 and 15.5 gallons of tetrahydrofuran (THF). The mixture was hydrogenated between 40–50° C. for 2 hours. At this time, analysis by TLC revealed that the reduction was essentially complete. The reaction was filtered through a 14" sparkler precoated with Celite and washed with 8 gallons of THF. The filtrate was transferred to a clean 100 gallon glass lined reactor, vacuum concentrated to a volume of 7 gallons and 21 gallons of ethyl acetate were charged. The suspension was atmospherically concentrated to a volume of 10 gallons and a pot temperature of 72° C. The suspension was cooled to 10° C., filtered on a 30" Lapp and washed with 2 gallons of ethyl acetate. After air drying at 55° C. this yielded a 3.9 kg (90%) of the above-depicted product (i.e., the free base).

STEP 6

A 100 gallon glass lined reactor was charged with 20 gallons of methanol and 3.7 kg (11.4 mol) of the product from step 5 (i.e., the free base). The suspension was heated to 60° C. and 1.7 kg (11.4 mol) of D-(−)-tartaric acid were charged. The resulting solution was heated to reflux (65°) for 3 hours after which a suspension formed. The suspension was cooled to 35° C., filtered on a 30" Lapp and washed with 1 gallon of methanol. The wet solids were charged to a 100 gallon glass lined reactor with 10 gallons of methanol. The suspension was stirred for 18 hours at 25° C. The suspension was filtered on a 30" Lapp and washed with 2 gallons of methanol. After air drying at 50° C. this yielded 2.7 kg (101%) of the above-depicted product (i.e., the tartaric acid salt of the free base (R-(+)-enantiomer)). This material was purified in the following manner:

A 100 gallon glass lined reactor was charged with 10.6 gallons of methanol and 2.67 kg (5.6 mol) of the above tartaric acid salt. The suspension was heated to reflux (80° C.) for 18 hours. The suspension was cooled to 30° C., filtered on a 30" Lapp and washed with 4 gallons of methanol. After air drying at 50° C., this yielded 2.05 kg (76.7%) of the above-depicted product (i.e., the tartaric acid salt of the free base).

STEP 7

A 55 liter nalgene tub was charged with 30 liters of water and 1056 g (12.6 mol) of sodium bicarbonate at 20° C. To the resulting solution was charged 2.0 kg (4.2 mol) of the product from step 6 (i.e., the tartaric acid salt of the free base). The suspension was stirred for 4 hours during which a great deal foaming occurred. After the foaming ceased, the suspension was filtered on a 32 cm funnel and washed with 1 gallon of water. After air drying at 50° C., this yielded 1.28 kg (93.5%) of the above-depicted product (i.e., the free base).

STEP 8

A 22 liter flask was charged with 1277 g (3.9 mol) of product from step 7 and 14 liters of water. The suspension was warmed to 30° C. and 375 g (3.9 mol) of methane sulfonic acid were charged. The resulting solution was warmed to 60° C., clarified by filtering through Celite and washed with 2 liters of water. The speck-free filtrate was concentrated under vacuum to a volume of 6 liters. The suspension was cooled to 0–5° C. and granulated for 1 hour. The product was filtered on a 18" filter funnel and washed with 635 ml of speck-free water. After air drying at 25° C. for 18 hours, this yielded 1646 g (88%) of the above-depicted product (i.e., the mesylate salt trihydrate).

We claim:

1. (1S,2S)-1-(4-hydroxyphenyl)-2-(4-hydroxy-4-phenylpiperidin-1-yl)-1-propanol methanesulfonate trihydrate.

2. A pharmaceutical composition for the treatment of a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, comprising an NMDA antagonizing effective amount of the trihydrate mesylate salt according to claim 1 and a pharmaceutically acceptable carrier.

3. A pharmaceutical composition for the treatment of a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, comprising an amount of the trihydrate mesylate salt according to claim 1 that is effective in treating each disorder and a pharmaceutically acceptable carrier.

4. A method of treating a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, comprising administering to said mammal an amount of the trihydrate mesylate salt according to claim 1 that is effective in treating such disorder.

5. A method of treating a disorder selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence in a mammal, comprising administering to said mammal an NMDA antagonizing amount of the trihydrate mesylate salt according to claim 1.

6. A method of treating Parkinson's disease in a mammal, comprising administering to said mammal a Parkinson's disease treating effective amount of a synergistic combination of the mesylate salt trihydrate according to claim 1 of (1S,2S)-1-(4-hydroxyphenyl)-2-(4-hydroxy-4-phenylpiperidin-1-yl)-1-propanol and an agent capable of restoring the balance of the excitatory feedback from the ventral lateral nucleus of the thalamus into the cortex.

7. A method of treating Parkinson's disease in a mammal, comprising treating said mammal with a Parkinson's disease treating effective amount of a synergistic combination of the mesylate salt trihydrate according to claim 1 and an excitatory feedback from enhancing agent selected from the group consisting of dopamine agonists, dopamine D1 agonists, dopamine D2 agonists, dopamine/β-adrenergic receptor agonists, dopamine/5-HT uptake inhibitor/5-HT-1A agonists, dopamine/opiate agonists, adrenoreceptor agonists, α2-adrenergic antagonist/dopamine agonists, α2-adrenergic/dopamine D2 agonists, dopamine uptake inhibitors, monoamine oxidase inhibitors, monoamine oxidase-B inhibitors, COMT inhibitors and levodopa.

8. A method of claim 7 wherein said excitatory feedback enhancing agent is levodopa.

9. A method according to claim 4, wherein the disorder being treated is Parkinson's disease.

10. A method according to claim 4, wherein the disorder being treated is traumatic brain injury or cerebral ischemia.

* * * * *